US012599568B2

(12) United States Patent
Lee et al.

(10) Patent No.: US 12,599,568 B2
(45) Date of Patent: Apr. 14, 2026

(54) SOFTGEL CAPSULES HAVING A FILL COMPOSITION COMPRISING MAGNESIUM OXIDE

(71) Applicant: CAPTEK SOFTGEL INTERNATIONAL, INC., Cerritos, CA (US)

(72) Inventors: Diana Paik Lee, Fullerton, CA (US); Hong Anh Nguyen, Westminster, CA (US); Timothy Brian Chiprich, Huntington Beach, CA (US); John Puckett, Cerritos, CA (US); Bibu Phillip George, Norwalk, CA (US)

(73) Assignee: CAPTEK SOFTGEL INTERNATIONAL, INC., Cerritos, CA (US)

( * ) Notice: Subject to any disclaimer, the term of this patent is extended or adjusted under 35 U.S.C. 154(b) by 346 days.

(21) Appl. No.: 18/296,020

(22) Filed: Apr. 5, 2023

(65) Prior Publication Data

US 2023/0310328 A1     Oct. 5, 2023

Related U.S. Application Data

(60) Provisional application No. 63/327,546, filed on Apr. 5, 2022.

(51) Int. Cl.
| | |
|---|---|
| *A61K 9/48* | (2006.01) |
| *A61K 9/50* | (2006.01) |
| *A61K 33/08* | (2006.01) |

(52) U.S. Cl.
CPC ............ *A61K 9/4858* (2013.01); *A61K 9/485* (2013.01); *A61K 9/5057* (2013.01); *A61K 33/08* (2013.01)

(58) Field of Classification Search
None
See application file for complete search history.

(56) References Cited

U.S. PATENT DOCUMENTS

| | | | |
|---|---|---|---|
| 5,614,217 A | 3/1997 | Chiprich et al. | |
| 5,891,470 A | 4/1999 | Rinaldi et al. | |
| 7,807,194 B2 | 10/2010 | Modliszewski et al. | |
| 2005/0152969 A1 | 7/2005 | Chiprich | |
| 2005/0220865 A1 | 10/2005 | Koleng et al. | |
| 2019/0091159 A1 | 3/2019 | Chiprich et al. | |
| 2019/0269623 A1 | 9/2019 | Bayless et al. | |
| 2022/0249455 A1* | 8/2022 | Ahmad | A61P 1/04 |

OTHER PUBLICATIONS

International Search Report and Written Opinion, Application No. PCT/US23/65360, Sep. 12, 2023, p. 7.
Blancquaert et al., Predicting and Testing Bioavailability of Magnesium Supplements, Nutrients, Jul. 20, 2019, p. 17, vol. 11 issue 7.
USP-NF Magnesium Oxide Capsules, 2025, USPC, pp. 4.
USP-NF <711> Dissolution, 2025, USPC, pp. 27.

* cited by examiner

*Primary Examiner* — Alton N Pryor
(74) *Attorney, Agent, or Firm* — FisherBroyles, LLP; Susan M. Oiler

(57) ABSTRACT

Softgel capsules have a fill composition that administers a 200 to 500 mg dose of magnesium from magnesium oxide and an outer sofgel gelatin shell. The composition includes 55 to 70% w/w of an edible oil, 2 to 8% w/w polysorbate 80, 0.5 to 2% w/w hydrophobic silica, and 0.2 to 4% w/w of a chelating agent for binding to magnesium. The softgel capsules have a dissolution according to USP <711> of greater than NLT 75% (Q).

12 Claims, 14 Drawing Sheets

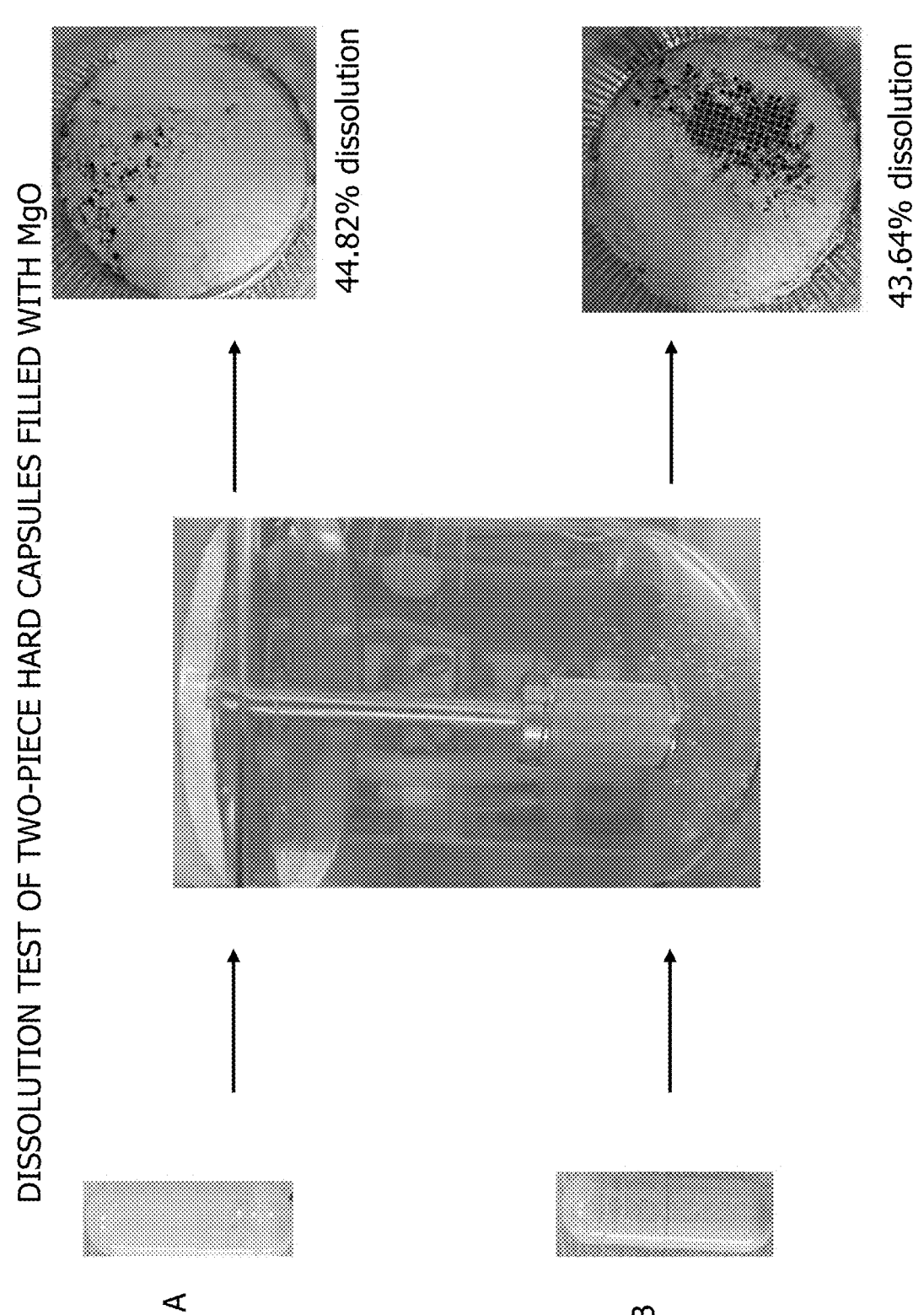
FIG. 1 (Prior Art Capsules)

FIG. 2

Dissolution Results for Commercial Products (Prior Art) using Basket Apparatus

| | Magnesium Citrate Softgel (125 mg Magnesium) | Magnesium Oxide Softgel (400 mg Magnesium) |
|---|---|---|
| Basket Apparatus Post-Dissolution Image | | |
| % of labeled claim | 0% | 0% |

FIG. 3

Dissolution Results for Commercial Products (Prior Art) using Paddle Apparatus

| | Magnesium Citrate Softgel (125 mg Magnesium) | Magnesium Oxide Softgel (400 mg Magnesium) |
|---|---|---|
| Paddle Apparatus Post-Dissolution Image | | |
| % of labeled claim | 0% | 0% |

FIG. 5

| | TRIAL 5 | TRIAL 6 | TRIAL 7 | TRIAL 8 | TRIAL 9 | TRIAL 10 | TRIAL 11 |
|---|---|---|---|---|---|---|---|
| Post-Dissolution Image | | | | | | | |
| % of labeled claim | 50.31% | 54.15% | 45.10% | 58.23% | 52.85% | 58.11% | 63.72% |

| | TRIAL 12 | TRIAL 13 | TRIAL 14 | TRIAL 15 | TRIAL 16 | TRIAL 17 | TRIAL 18 |
|---|---|---|---|---|---|---|---|
| Post-Dissolution Image | | | | | | | |
| % of labeled claim | 68.85% | 81.76% | 82.50% | 90.40% | 95.75% | 91.81% | 93.94% |

FIG. 6

| Post-Dissolution Image | TRIAL 20 | TRIAL 21 | TRIAL 22 |
|---|---|---|---|
| % of labeled claim | 97.5% | 86.7% | Failed |

FIG. 7

Trial 20 Bulk Stability Result at Ambient Condition

| Time Point | 3 Month | 4 Month | 6 Month |
|---|---|---|---|
| Trial 20 (Ambient) Post-Dissolution Image | | | |
| % of labeled claim | 97.5% | 94.3% | 43.5 % |

FIG. 9

Trial 21 Bulk Stability Result at Ambient Condition (Basket Apparatus)

| | 3 Month | 4 Month | 6 Month |
|---|---|---|---|
| Trial 21 (Ambient Condition) Post-Dissolution Image | | | |
| % of labeled claim | 86.7% | 88.9% | 83.5% |

Trial 21 - Bulk Stability at Ambient Condition for 6 Month (Basket Apparatus)

FIG. 11

Trial 21 Bottle Stability Result at Intermediate Condition (Basket Apparatus)

| Trial 21 (Intermediate Condition) | 1 Month | 2 Month | 3 Month |
|---|---|---|---|
| Post-Dissolution Image | | | |
| % of labeled claim | 88.7 % | 97.6 % | 79.1 % |

FIG. 13

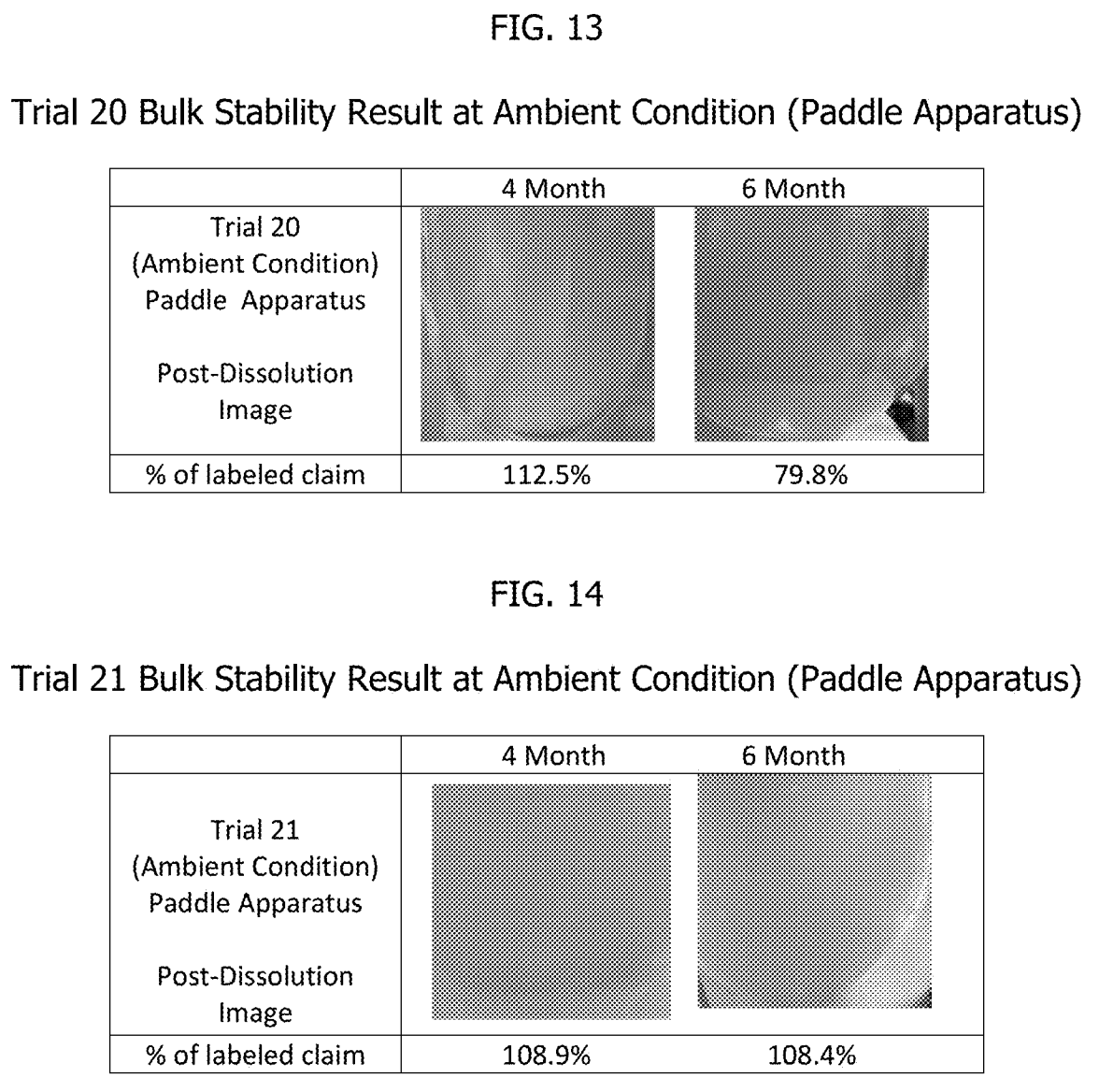

Trial 20 Bulk Stability Result at Ambient Condition (Paddle Apparatus)

| Trial 20<br>(Ambient Condition)<br>Paddle Apparatus | 4 Month | 6 Month |
|---|---|---|
| Post-Dissolution<br>Image | | |
| % of labeled claim | 112.5% | 79.8% |

FIG. 14

Trial 21 Bulk Stability Result at Ambient Condition (Paddle Apparatus)

| Trial 21<br>(Ambient Condition)<br>Paddle Apparatus | 4 Month | 6 Month |
|---|---|---|
| Post-Dissolution<br>Image | | |
| % of labeled claim | 108.9% | 108.4% |

Trial 21 Bulk Stability Result at Ambient Condition (40°C/75%RH), Paddle Apparatus

SOFTGEL CAPSULES HAVING A FILL COMPOSITION COMPRISING MAGNESIUM OXIDE

TECHNICAL FIELD

The present disclosure relates generally to the field of softgel capsules, and more particularly to softgel capsules filled with magnesium oxide in an edible oil with polysorbate 80, hydrophobic silica, and a chelating agent. The sofgel capsules passes the USP <711> dissolution test following USP monograph for Magnesium Oxide Capsule.

BACKGROUND

Many Americans don't get enough magnesium in their diets. Magnesium is available in nuts, seeds, whole grains, beans, leafy vegetables, milk, yogurt, and fortified foods. Yet, some people turn to a supplement to ensure the intake of a daily dose of magnesium. Magnesium can support muscle and nerve function, support energy production, improve sleep, and relieve anxiety and constipation. Low magnesium levels typically do not have negative health consequences; however, chronically low levels can increase the risk of high blood pressure, heart disease, type 2 diabetes, and osteoporosis.

Many supplements for the intake of magnesium are available on the market. The supplements can be in the form of a powder, liquid, tablet, or hard capsules and often contain a mixture of magnesium salts such as magnesium glycinate, magnesium citrate, magnesium chloride, magnesium sulfate, magnesium malate, and magnesium oxide. These magnesium salts differ in terms of their solubility. For example, organic salts, such as magnesium citrate and glycinate have been shown to have a higher water solubility than magnesium oxide (MgO).

Magnesium oxide is an inorganic salt of magnesium. Magnesium oxide is of interest because it provides a higher loading of elemental magnesium. However, magnesium oxide exhibits limited bioavailability because of its poor solubility, which is a problem. Referring to FIG. 1, two two-piece hard capsules were filled with MgO and put through a dissolution test. Hard capsule A had a load of about 350 mg of magnesium (about 620 mg MgO), HA grade Dead Sea Periclase. Hard capsule B had a load of about 350 mg of magnesium (about 620 mg MgO), heavy powder "LL" from Tomita Pharma. The dissolution test was performed according to USP <711>'s test procedure, which utilizes apparatus 1 (basket apparatus) and apparatus 2 (paddle apparatus) containing 900 ml of 0.1 N HCl run at 100 rpm for 45 minutes. The amount of MgO dissolved is determined using Atomic Absorption (AA) spectrophotometry at a wavelength of 285.2 nm using a filtered portion of the solution under test, diluted with dissolution medium. A standard curve is generated using a magnesium standard solution of known concentration in the same medium. The assay testing for magnesium was performed according to the current USP monograph for Magnesium Oxide Capsule. An acceptable result is not less than (NLT) 75% (Q) of the labeled amount of MgO dissolved. Hard capsule A and B both had a dissolution of about 44%, which is far below the acceptable result of 75%.

Also, two commercial products of magnesium softgel, 125 mg Magnesium Citrate and 400 mg Magnesium Oxide softgels, were tested for dissolution using both basket and paddle apparatus. Results of the tests are provided in FIGS. 2 and 3. The magnesium citrate is known to have a higher water solubility compared to the magnesium oxide form. Both products did not dissolve any magnesium ion during the dissolution test with the basket apparatus or the paddle apparatus.

Both hard capsules and softgel capsules are orally administrable. Hard capsules are more stable than soft gelatin capsules and are less prone to react with the shell matrix because hard capsules are made of unplasticized or low-plasticized gelatin and water to form a stiff capsule that is typically filled with either powder or liquid.

Softgel capsules are desirable over hard capsules because of consumer preferences, improved bioavailability, speed of manufacturing, enhanced drug stability due to reduced exposure of the active ingredient to oxygen, dose uniformity, and product differentiation through capsule color and shape. Applicant desires to encapsulate magnesium oxide in softgel capsules to take advantage of these benefits. However, preliminary dissolution tests of softgel capsules filled with magnesium oxide (MgO) evidenced low solubility and cross-linking. The softgel capsule shell contains a considerable amount of water, and MgO reacts with the water from the shell, especially under high temperature and humidity and may form $Mg(OH)_2$, which is less water soluble and prolongs the dissolution time. In addition, high temperature and humidity facilitated cross-linking of the capsule shell arising from gelatin polymerization, which can significantly slow the dissolution rate.

Applicant is unaware of any softgel capsules having magnesium from magnesium oxide in a sufficient quantity to provide the daily dosage of magnesium in one capsule that meets or exceeds the USP <711> dissolution test and following USP monograph for Magnesium Oxide Capsule.

There is a need for orally administrable softgel capsules for those persons in need of a magnesium supplement that has high magnesium loading provided by magnesium oxide and dissolution of magnesium oxide that passes the USP <711> test.

SUMMARY

In all aspects, disclosed herein are softgel capsules have a fill composition that administers a 200 to 500 mg dose of magnesium from magnesium oxide and an outer softgel gelatin shell. The composition includes 55 to 70% w/w of an edible oil, 2 to 8% w/w polysorbate 80, 0.5 to 2% w/w hydrophobic silica, and 0.2 to 4% w/w of a chelating agent for binding to magnesium. The softgel capsules have a dissolution according to USP <711> of greater than NLT 75% (Q), more preferably greater than NLT 85% (Q). The chelating agent can be an ethylenediaminetetraacetic acid (EDTA) salt and/or a weak acid. When the weak acid is present, it is selected from the group consisting of ascorbic acid, aspartic acid, citric acid, glutamic acid, pyridoxine HCl, and ciombinations thereof. In one embodiment, the chelating agent includes an ethylenediaminetetraacetic acid (EDTA) salt and a weak acid in a ratio of 2:1 to 2.5:1. The polysorbate 80 can be present as about 6% to about 6.7% w/w of the fill composition.

In an example embodiment, the edible oil comprises a medium-chain triglyceride oil, and the fill composition can have a formulation of 50 to 65% w/w of a medium-chain triglyceride oil; 5.8 to 6.8% w/w polysorbate 80; 1 to 2% w/w hydrophobic silica; and 0.5 to 4% w/w of a chelating agent for binding to magnesium. The softgel capsules have a dissolution according to USP <711> of greater than NLT 75% (Q) after three months in an intermediate set at 30° C./65% RH and one month in an accelerated condition chamber set at 40° C. and 75% relative humidity, and greater than NLT 85% (Q) after six month at ambient condition. Moreover, the the softgel capsules have a dissolution according to USP <711> with Apparatus 2 of greater than NLT 100% (Q) after six month at ambient condition and three months in an intermediate set at 30° C./65% RH; and greater than NLT 75% after a 4-month period in an accelerated condition chamber set at 40° C. and 75% relative humidity. This example embodiment can have a chelating agent that includes an ethylenediaminetetraacetic acid (EDTA) salt and/or a weak acid. The weak acid can be selected from the group consisting of ascorbic acid, aspartic acid, citric acid, glutamic acid, pyridoxine HCl, and combinations thereof. Further, the chelating agent can be an ethylenediaminetetraacetic acid (EDTA) salt and a weak acid in a ratio of 2:1 to 3:1.

BRIEF DESCRIPTION OF THE DRAWINGS

FIG. 1 is a schematic flowchart of images from a dissolution test of two-piece hard capsules filled with magnesium oxide (MgO).

FIG. 2 is a chart of images and data from dissolution tests using a basket apparatus for 125 mg magnesium from a magnesium citrate softgel and 400 mg magnesium from MgO in softgel capsules.

FIG. 3 is a chart of images and data from dissolution tests using a paddle apparatus of commercial products for 125 mg magnesium from a magnesium citrate softgel and 400 mg magnesium from MgO in softgel capsules

FIG. 5 is a chart of images and data from the dissolution test of 400 mg magnesium from MgO in softgel capsules for trials 5 through 18.

FIG. 6 is a chart of images and initial test data from the dissolution test of 400 mg magnesium from MgO in softgel capsules for trials 20, 21, and 22.

FIG. 7 is a chart of images and stability data for dissolution test using a basket apparatus from 3-month, 4-month, and 6-month at ambient condition for Trial 20.

FIG. 9 is a chart of images and stability data from the dissolution test using a basket apparatus from 3-month, 4-month, and 6-month at ambient condition for Trial 21.

FIG. 11 is a chart of image and stability data from the dissolution test using a basket apparatus from 1-month, 2-month, and 3-month at intermediate condition (30° C./65% RH) for Trial 21.

FIG. 13 is a chart of images and stability data for dissolution test using a paddle apparatus from 4 and 6 months at ambient condition for Trial 20.

FIG. 14 is a chart of images and stability data for dissolution test using a paddle apparatus from 4 and 6 months at ambient condition for Trial 21.

DETAILED DESCRIPTION

Figure 4:
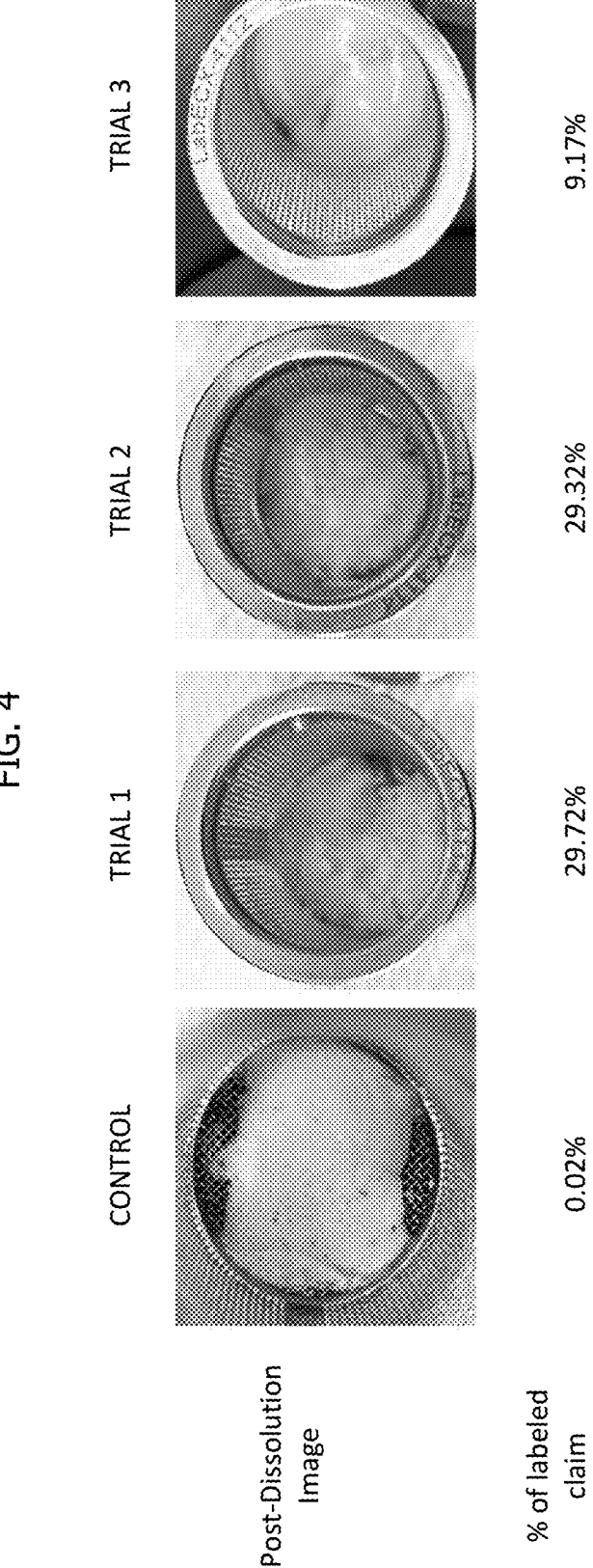
FIG. 4 is a chart of images and data from dissolution tests of 400 mg magnesium from MgO in softgel capsules.
Figure 8:
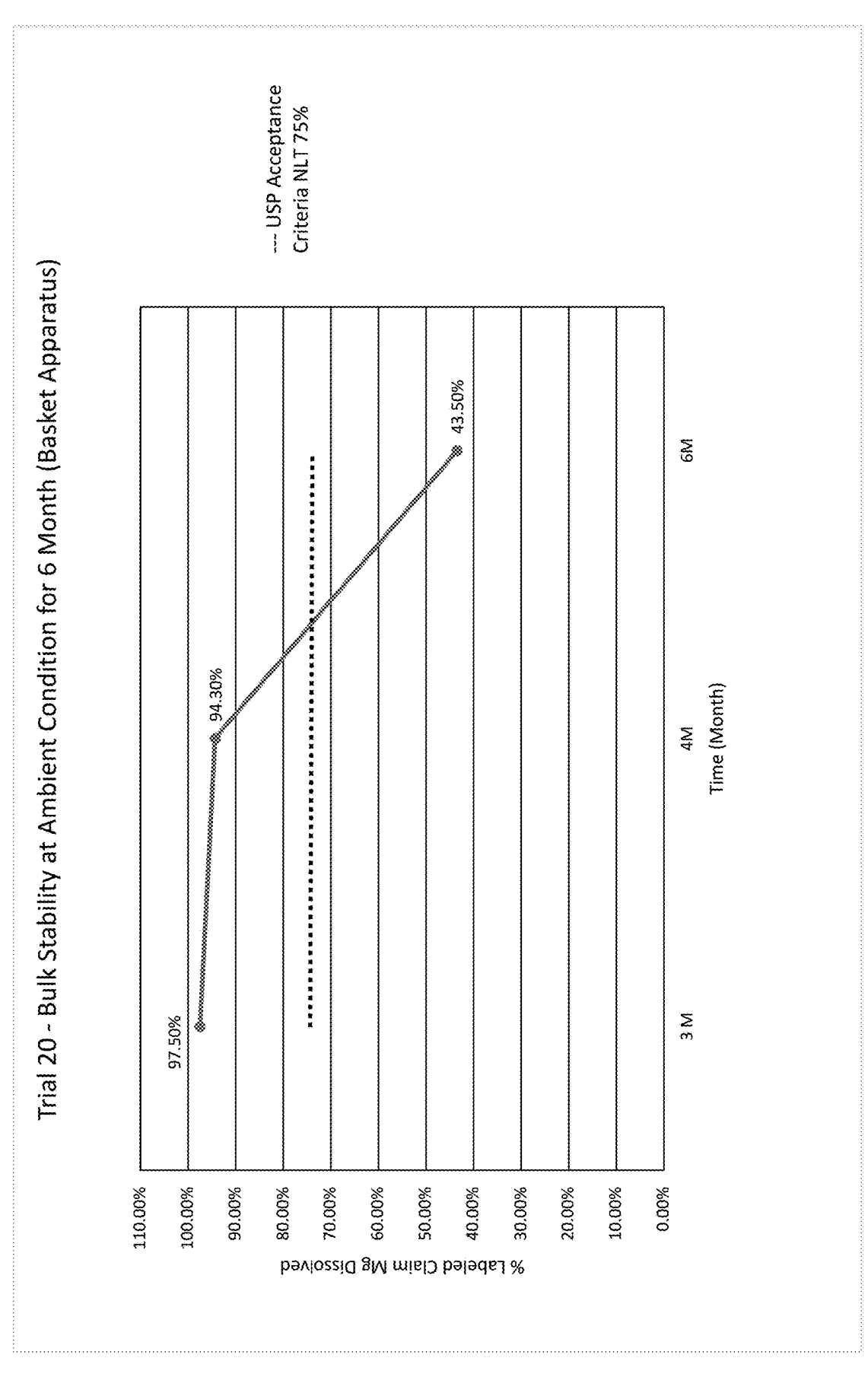
FIG. 8 is a stability plot of the data from FIG. 7 for Trial 20.
Figure 10:
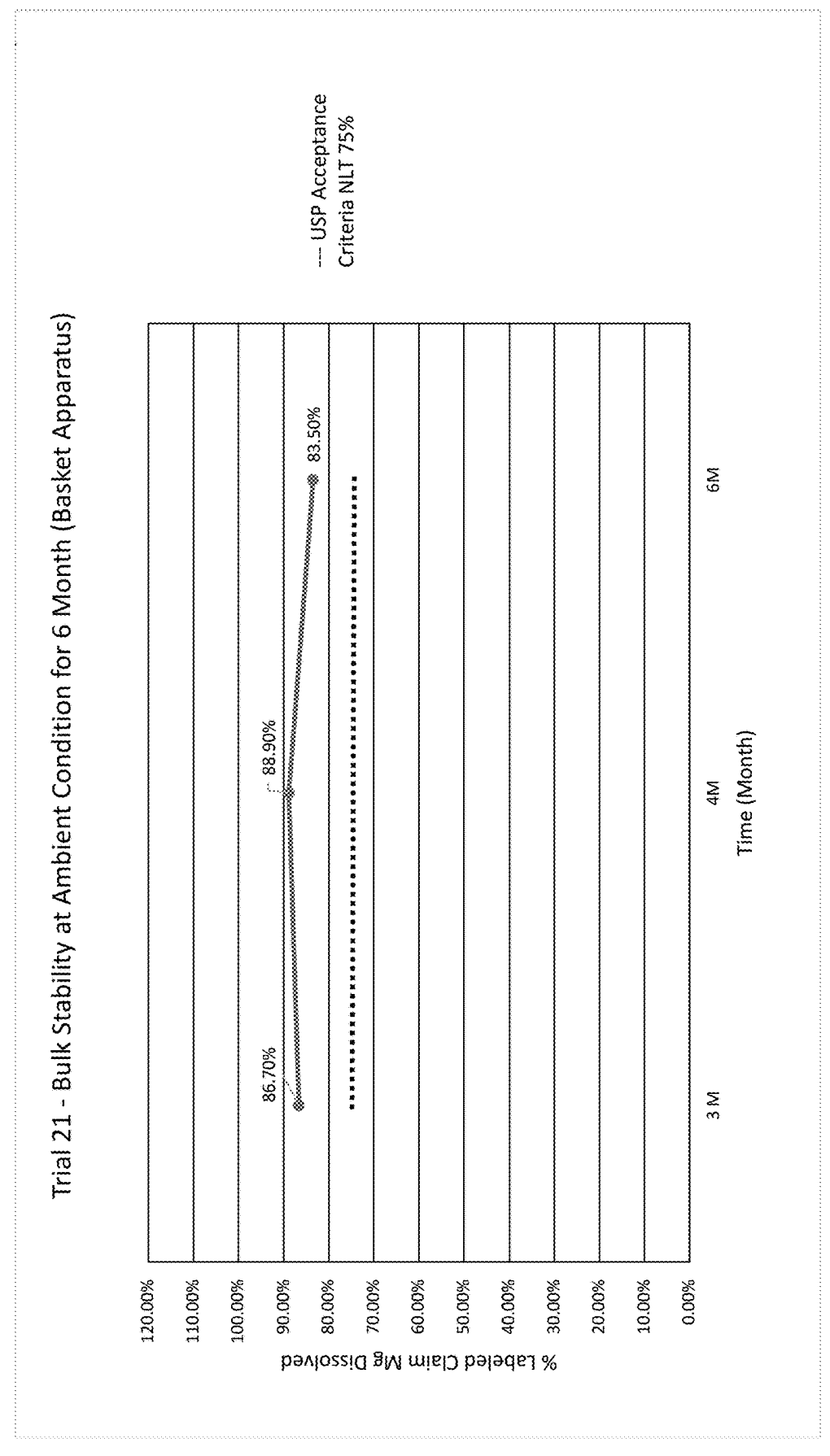
FIG. 10 is a stability plot of the data from FIG. 9 for Trial 21.
Figure 12:
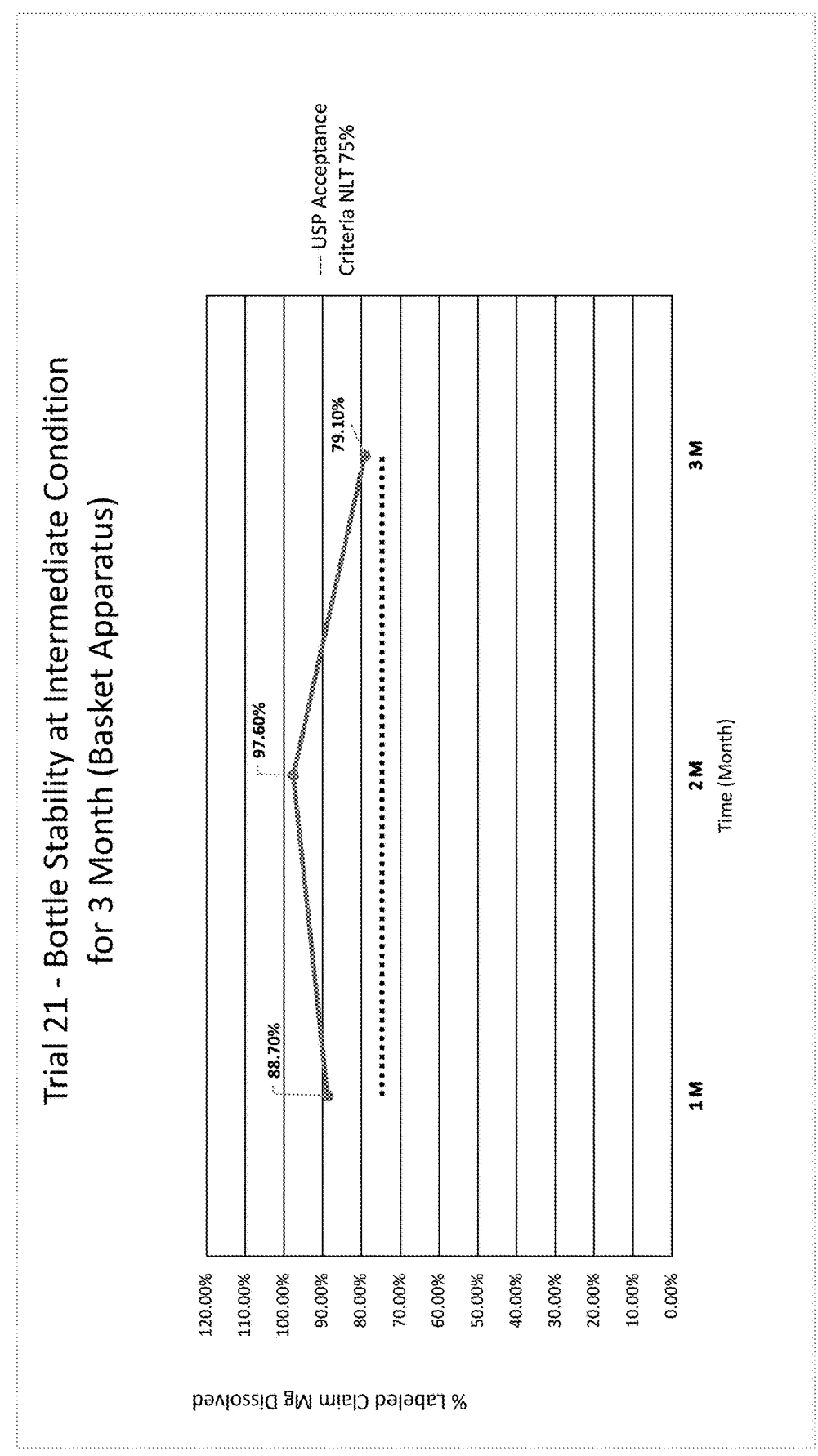
FIG. 12 is a stability plot of the data from FIG. 11 for Trial 21.
Figure 15:
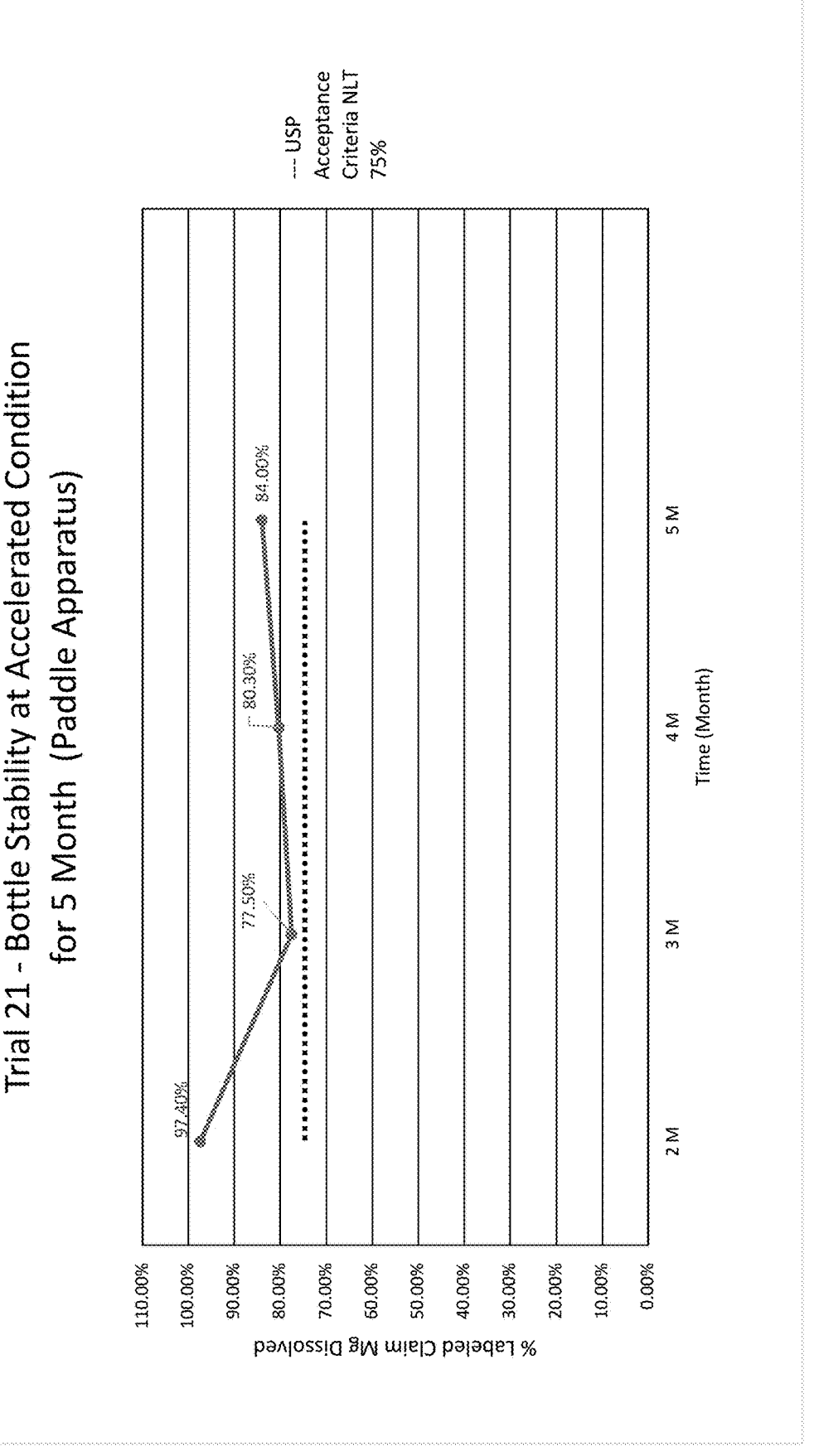
FIG. 15 is a stability plot of 5 months of stability data for the dissolution test using a paddle apparatus at the accelerated condition for Trial 21.
Figure 16:
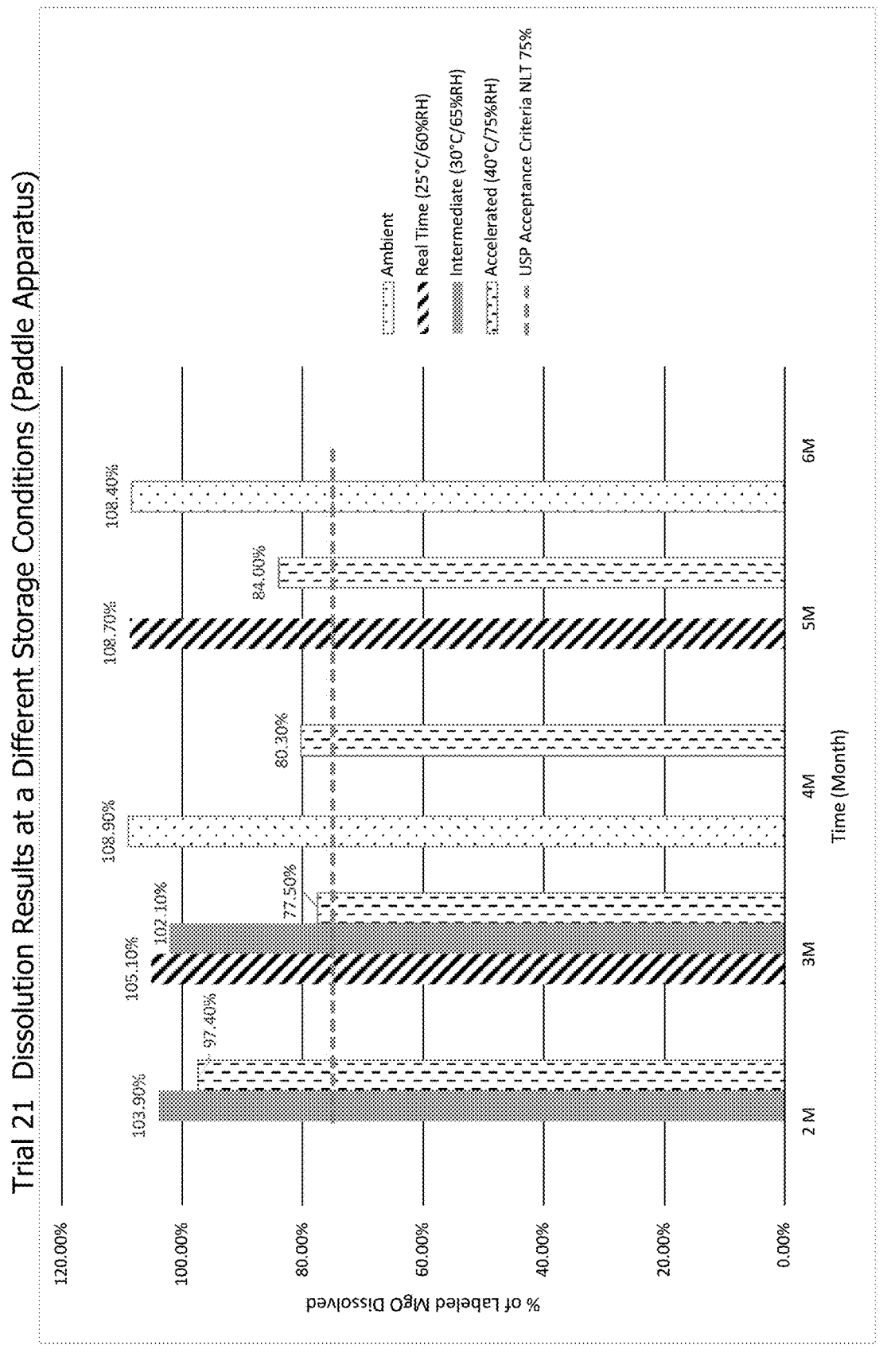
FIG. 16 is a bar graph of the influence of storage conditions on an MgO dissolution profile in a paddle apparatus during a 6 months stability study.

Ranges can be expressed herein as from "about" one particular value, and/or to "about" another particular value. "About" as used herein means plus or minus 5% of a numerical value, or more preferably plus or minus 2%. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. Percentages for concentrations are typically % by weight/weight unless expressly stated otherwise.

The following description and drawings are illustrative and are not to be construed as limiting. Numerous specific details are described to provide a thorough understanding of the disclosure. However, in certain instances, well-known or conventional details are not described to avoid obscuring the description. Reference to an "embodiment" or "example embodiment" means that a particular feature, structure, or characteristic described in connection with the embodiment is included in at least one embodiment of the disclosure.

Provided herein are softgel capsules filled with magnesium oxide in an edible oil with polysorbate 80, hydrophobic silica, and a chelating agent encapsulated within an outer softgel shell that passes the USP <711> dissolution test at NLT 75% of the labeled claim. The softgel capsules have 400 mg of magnesium from MgO.

As used herein, a "softgel capsule" refers to a pharmaceutical device having a shell formed of highly plasticized soft elastic shell material to define at least one chamber for a dosage of fill material. The fill material can be a liquid, suspended powder in a liquid, or a semisolid. The softgel capsule can have a seam or can be seamless, depending upon the method of manufacturing. Seamed softgel capsules can be made using a rotary die encapsulation machine. Seamless softgel capsules can be made by either coacervation or by the "drop method" using concentric nozzles (i.e., a coextrusion process without mechanical shaping). The shell material can be animal gelatin plasticized with polyhydric alcohols (e.g., glycerol, sorbitol, maltitol, etc.) or one or more vegetarian capsule-forming materials such as starches, modified starches, carrageenan and alginates or similar polymers, with or without polyhydric alcohol plasticizers. Any softgel shell material is suitable herein. Examples of softgel shells are described in U.S. Pat. Nos. 5,614,217; 7,807,194; U.S. patent publication US 2005/0152969; and U.S. patent publication US 2019/0269623, the contents of each of which is hereby incorporated by reference in their entirety.

Softgel capsules can provide distinct advantages over more traditional dosage forms such as tablets, hard-shell capsules, and liquids. These advantages include patient compliance and consumer preference, improved bioavailability, speed of product development in many cases, shortened manufacturing time, enhanced drug stability due to less exposure of the active ingredient to oxygen, dose uniformity, and product differentiation, for example through novel shapes.

The fill composition includes 55-70% w/w of an edible oil, 2-8% w/w polysorbate 80, 0.5-2% w/w hydrophobic silica, and optionally 0.2 to 4% w/w of a chelating agent for binding to magnesium. When the chelating agent is present, higher dissolution percentages are achieved, especially with high magnesium doses. The polysorbate may be more preferably in a range of about 6% to about 6.7% w/w of the fill composition. In one embodiment, the fill composition includes 50-65% w/w of an edible oil, 5.8-6.8% w/w polysorbate 80, 0.5 to 4% w/w of a chelating agent for binding to magnesium.

One example of an edible oil is a medium-chain triglyceride (MCT) oil. MCT oils are triglycerides with two or three fatty acids having an aliphatic tail of 6-12 carbon atoms, i.e., medium-chain fatty acids. In one embodiment, the MCT oil can be from palm kernel oil and/or coconut oil. Typically, MCT oil is separated from the coconut or palm kernel oil through a process called fractionation. Any other edible oil can be used alone or in combination with the MCT oil. Some examples of sources of oils and fats include, optionally fractions of, coconut oil, palmkernel oil, palm oil, marine oils, lard, tallow fat, butter fat, soybean oil, safflower oil, cotton seed oil, rapeseed oil, poppy seed oil, corn oil, sunflower oil, olive oil, algae oil and blends thereof. Hydrogenation may be used to alter the degree of unsaturation of the fatty acids and as such to alter the fatty acid composition.

Hydrophobic silica is a form of silicon dioxide that has hydrophobic groups chemically bonded to the surface. The hydrophobic groups are normally alkyl or polydimethylsiloxane chains. Hydrophobic silica was selected add as an additive to make the entire fill matrix more hydrophobic and to lessen the interaction between the fill and the water in a shell. It minimizes the reaction between shell moisture and magnesium oxide and may inhibit the formation of magnesium hydroxide.

The chelating agent includes an ethylenediaminetetraacetic acid (EDTA) salt and/or one or more weak acids. EDTA is a chelating and sequestering agent that inhibits undesirable reactions in the fill matrix. EDTA reacts with magnesium to form a complex with the magnesium ions, which is a stable, water-soluble complex. The resulting structure (chelated) immobilizes the magnesium ions and prevents them from reacting with other components in the fill and shell matrices, especially water. Described another way, the magnesium ions are trapped by the chelating agent prior to filling or being encapsulated in the softgel, thereby inhibiting the hydration of magnesium oxide.

The chelating agent binds to the magnesium ions from MgO to keep the MgO from reacting with water to form magnesium hydroxide. Examples of the EDTA salt include, but are not limited to, calcium disodium EDTA, diammonium EDTA, dipotassium EDTA, disodium EDTA, TEA-EDTA, tetrasodium EDTA, tripotassium EDTA, and trisodium EDTA. In all embodiments, the chelating agent can include an EDTA salt and a weak acid. The weak acid(s) are selected from the group consisting of ascorbic acid, aspartic acid, citric acid, glutamic acid, pyridoxine HCl, and combinations thereof.

The invention will now be described in detail by way of reference to the following examples. It is to be understood that one, some, or all properties of the various embodiments and examples described herein may be combined to form other embodiments.

EXAMPLES

Dissolution of magnesium oxide was tested, as noted in the background section, with hard capsules to establish a baseline for the dissolution of MgO. In all examples below conventional techniques of mixing were used and hand filled capsules were made for these preliminary tests. Air-filled softgel capsules having a shell of 150 Bl Bovine Bone Gelatin, 55% plasticized with Glycerin were used to create the trial softgel capsules. Wet air-filled capsules were individually injected with a known weight of one of the fill materials described in the examples below. Then, the open tip of each filled softgel capsule was sealed closed with heating. The capsules were dried in an R&D drying chamber set with a relative humidity of 10-20% for 2-3 days. Thereafter, the USP <711> dissolution test using a basket apparatus was performed.

400 mg Magnesium from MgO Softgel Capsules

Next, a known fill material of MCT oil as the main delivery vehicle and rapeseed lecithin was used as an emulsifier for magnesium oxide within a softgel capsule. This softgel capsule had a dissolution test result of 0.02% and became the Control formulation noted in FIG. 4. Since this base fill had such poor performance other base fill materials were selected for Trials 1-3— Polysorbate 80 was selected as an emulsifier instead of using lecithin. The main filler used in Trial 1 and 2 was MCT oil; and Trial 3 and 4 was polyethylene glycol 400.

TABLE 1

|  | Control | TRIAL 1 | TRIAL 2 | TRIAL 3 | TRIAL 4 |
|---|---|---|---|---|---|
| Magnesium oxide | 54.90 | 52.08 | 50.43 | 46.52 | 45.63 |
| MCT Oil | 41.39 | 44.46 | 43.25 | — | — |
| Rapeseed Lecithin | 3.70 | — | — | — | — |
| Polysorbate 80 | — | 3.26 | 6.32 | — | 1.90 |
| PEG 400 | — | — | — | 53.48 | 52.47 |
| Fill weight (mg) | 1308 | 1380 | 1425 | 1545 | 1575 |
| AA Results (%) | 0.02% | 29.72% | 29.32% | 9.17% | 7.85% |

(all values are % w/w unless noted otherwise)

The dissolution test results for Trials 1-4 are presented in Table 1. Trials 1 and 2 having the polysorbate 80 and MCT oil had a dissolution of about 29%, which while far better than the 0.02% of the Control, still fell far short of the NLT 75% (Q) to meet USP <711>. The hydrophilic PEG 400 base fill, with and without polysorbate 80, only had a dissolution of about 8-9%.

Improve the Dissolution of 400 mg Magnesium Form MgO in Polysorbate 80/MCT Oil Base Fill.

EDTA as a chelating agent was added to help prevent insolubility of the magnesium by binding to the magnesium as described herein and preventing the hydration reaction that forms magnesium hydroxide. Various weak acids were tested to see if any would improve the dissolution. Citric acid, ascorbic acid and pyridoxine hydrochloride were selected to enhance the solubility of magnesium. Hydrophobic silica was selected add as a suspending agent and additive to form a layer between the shell and fill composition to minimize moisture migration and decrease the hydration of magnesium oxide.

TABLE 2

| TRIAL # | 5 | 6 | 7 | 8 | 9 | 10 | 11 |
|---|---|---|---|---|---|---|---|
| Magnesium oxide | 38 | 38 | 38 | 38 | 38 | 38 | 38 |
| MCT Oil | 58 | 58 | 58 | 58 | 58 | 58 | 58 |
| Polysorbate 80 | 2.12 | 2.12 | 2.12 | 2.38 | 2.38 | 2.38 | 2.38 |
| Hydrophobic silica | 1.51 | 1.51 | 1.51 | — | — | 0.53 | 0.53 |
| EDTA 0.5%/ | — | 0.7 | 0.7 | 1.26 | 1.26 | 1.26 | 1.26 |

TABLE 2-continued

| TRIAL # | 5 | 6 | 7 | 8 | 9 | 10 | 11 |
|---|---|---|---|---|---|---|---|
| citric acid 0.2% | | | | | | | |
| Vitamin C (ascorbic acid) | — | — | 0.14 | — | — | — | — |
| Vitamin B6 (pyridoxine HCl) | — | — | — | — | 1 | — | 1 |
| AA Results (%) | 50.31 | 54.15 | 45.10 | 58.23 | 52.85 | 58.11 | 63.72 |

(all values are % w/w, except for the AA Result)

Based on the Dissolution test ("AA") results, as compared to Table 1, the addition of the hydrophobic silica and EDTA/citric acid chelating agent improved the dissolution test results. The percentages improved by at least 15%, 20%, and 30%, but not of the softgel capsules passed the USP <711> dissolution test using Apparatus 1. Trial 7 which had the ascorbic acid, had the lowest dissolution percentage, and Trial 11, which had hydrophobic silica and Vitamin B6, had the highest dissolution percentage. Based on these results, more trials were performed.

TABLE 3

| TRIAL # | 12 | 13 | 14 | 15 | 16 | 17 | 18 |
|---|---|---|---|---|---|---|---|
| Magnesium oxide | 38.25 | 38.06 | 36.97 | 36.87 | 35.44 | 35.91 | 35.25 |
| MCT Oil | 58.55 | 58.26 | 56.59 | 56.44 | 54.24 | 54.96 | 53.96 |
| Polysorbate 80 | 2.66 | 2.65 | 2.57 | 5.70 | 5.97 | 5.47 | 5.94 |
| Hydrophobic silica | 0.53 | 1.03 | 0.51 | 1.00 | 0.96 | 0.50 | 1.47 |
| EDTA | — | — | 0.97 | — | 0.93 | 0.90 | 0.92 |
| Citric Acid | — | — | 0.43 | — | 0.48 | 0.46 | 0.48 |
| Vitamin B6 (pyridoxine HCl) | — | — | 2.57 | — | 2.00 | 1.80 | 1.99 |
| AA Results (%) | 68.85 | 81.76 | 82.50 | 90.40 | 95.75 | 91.81 | 93.94 |

(all values are % w/w, except for the AA Result)

Based on the test results from Trial 12 through 18, it was concluded that the increase of polysorbate 80 and pyridoxine HCl enhanced the solubility, and the hydrophobic silica was adjusted to boost the solubility.

Trial 19, presented below, is the revised formulation from the Trial 18 by adjusting the amount of MCT oil to fit into one softgel. The test result met the NLT 75% requirement.

TABLE 4

| | TRIAL 19 |
|---|---|
| Magnesium oxide | 40.04 |
| MCT Oil | 48.82 |
| Polysorbate 80 | 6.42 |
| Hydrophobic silica | 1.06 |
| EDTA | 1.00 |
| Citric Acid | 0.51 |
| Vitamin B6 (pyridoxine HCl) | 2.15 |
| AA Results (%) | 79.92 |

With the success of the magnesium 400 mg from MgO softgel capsules in Trial 19, pilot batches were manufactured for stability studies.

Pilot Batch: 400 mg magnesium from MgO softgel capsule

For these pilot batches, the gelatin and vegetarian softgel capsules described above were used. Each of the capsules was a size 25 oblong capsule. The formulations selected for the pilot batches are outlined in Table 5 and were made using conventional techniques.

TABLE 5

| | TRIAL 20 | TRIAL 21 | TRIAL 22 |
|---|---|---|---|
| Magnesium oxide | 39.75 | 38.89 | 38.89 |
| MCT Oil | 50.88 | 49.78 | 49.78 |
| Polysorbate 80 | 6.68 | 6.54 | 6.54 |
| Hydrophobic silica | 1.11 | 1.08 | 1.08 |
| EDTA disodium | 1.04 | 1.02 | 1.02 |
| Citric acid | 0.54 | 0.52 | 0.52 |
| Vitamin B6 (pyridoxine HCl) | — | 2.16 | 2.16 |
| Dissolution Test Result (average) | Passed (97.5%) | Passed (86.7%) | Failed |
| Shell formulation | Gelatin | | Vegetarian |

(all values are % w/w unless stated otherwise)

Trial 22 failed the dissolution test. Here, the vegetarian softgel capsule was only partially dissolved in the 45 minutes test period prescribed by USP <711> using Apparatus 1 and the testing medium was still generally clear. Trials 20 and 21 passed the dissolution test. The average dissolution for Trial 20 was 97.5% (103.9%; 91.1%; 87.7%; 108.2%; 112.0%; 82.3%). The average dissolution for Trial 21 was 86.7% (89.9%; 90.0%; 92.6%; 85.8%; 85.0%; 76.7%).

Bulk Stability Study at Ambient Condition of Trial 21 and 22

Capsules were packaged into a polyethylene bag, sealed with a zip-tie, placed in a single wall carboard carton, and stored at ambient conditions.

The dissolution data from Trial 20 and 21 provided below in Table 6 and Table 7 is for a bulk stability at ambient condition according to USP <711> using a Basket Apparatus and a Paddle Apparatus, respectively.

TABLE 6

Trial 20 and 21 Dissolution Result USP <711> with a Basket Apparatus
Bulk Stability Result at
Ambient, Dissolution <711> with a Basket Apparatus

| Time Point | 3 Month | 4 Month | 6 Month |
|---|---|---|---|
| Trial 20 | 97.5% | 94.3% | 43.5% |
| Trial 21 | 86.7% | 88.9% | 83.5% |

TABLE 7

Trial 20 and 21 Dissolution Result per USP <711> with a Paddle Apparatus
Bulk Stability Result at
Ambient, Dissolution <711> with a Paddle Apparatus

| Time Point | 4 Month | 6 Month |
|---|---|---|
| Trial 20 | 112.5% | 79.8% |
| Trial 21 | 108.9% | 108.4% |

Trial 20 capsules showed a significant reduction in dissolution between 4 months and 6-month period in basket apparatus, the result was reduced from 94.3% to 43.5%. The result was 112.5% at 4 month and 79.8% at 6 month with the basket apparatus.

Trial 21 capsules were relatively stable during the 6 months stability, the result from 3 month, 4 month and 6 months were 86.7%, 88.9% and 83.5% in the basket apparatus; and 108.9% at 3 month and 108.4% at 4 month in the paddle apparatus.

Bottle Stability at Controlled Condition of Trial 20 and 21

45 capsules from Trial 20 and Trial 21 were placed into a white HDPE bottle, sealed with heat induction, and stored in three (3) storage conditions, 25° C./60% relative humidity (RH) (real-time), 30° C./65% RH (intermediate), 40°

C./75% RH (accelerated) for stability. The samples were tested for dissolution per USP <711> using the Basket Apparatus and the Paddle Apparatus for a 3 month period.

TABLE 8

| Trial 20 Dissolution Result with Apparatus 1 (basket) | | | |
| Trial 20 | | | |
| Time point | 1 month | 2 month | 3 month |
| Real Time (25° C./60% RH) | — | — | Failed |
| Intermediate (30° C./65% RH) | 95.6% | Failed | — |
| Accelerated (40° C./75% RH) | Failed | — | — |

— Test Not Performed.

TABLE 9

| Trial 20 Dissolution Result with Apparatus 2 (paddle) | | | |
| Trial 20 | | | |
| Time point | 2 month | 3 month | 5 month |
| Real Time (25° C./60% RH) | — | 81.0% | Failed |
| Intermediate (30° C./65% RH) | 101.8% | Failed | — |
| Accelerated (40° C./75% RH) | Failed | — | — |

— Test Not Performed.

TABLE 10

| Trial 21 Dissolution Result with Apparatus 1 (Basket) | | | | |
| Trial 21 | | | | |
| Time point | 1 month | 2 month | 3 month | 5 month |
| Real Time (25° C./60% RH) | — | — | 79.4% | 98.2% |
| Intermediate (30° C./65% RH) | 88.7% | 97.6% | 79.1% | — |
| Accelerated (40° C./75% RH) | 84.4% | Failed | Failed | — |

— Test Not Performed

TABLE 11

| Trial 21 Dissolution Result with Apparatus 2 (paddle) | | | | |
| Trial 21 | | | | |
| Time point | 2 month | 3 month | 4 month | 5 month |
| Real Time (25° C./60% RH) | — | 105.1% | — | 108.7% |
| Intermediate (30° C./65% RH) | 103.9% | 102.1% | — | — |
| Accelerated (40° C./75% RH) | 97.4% | 77.5% | 80.3% | 84.0% |

— Test Not Performed

Trial 21 had NLT 80% without showing a considerable reduction in dissolution during 6 months of bulk stability at ambient condition using Apparatus 1 (Basket).

Trial 21 met the requirement at a greater than 100% with Apparatus 2 (paddle) for 6-month bulk stability at ambient conditions.

Trial 20 did not meet the requirement after one month period at intermediate and accelerated conditions.

Trial 21 met the NLT 75% requirement for a 3-month period at real time and intermediate conditions using Apparatus 1 (basket); it also met the requirement at NLT 100% dissolution with Apparatus 2 (paddle) method from the same conditions.

Trial 21 met the NLT 75% requirement at 1 month of the accelerated condition using the Basket Apparatus; and a 4-month period in an accelerated condition with the Paddle Apparatus.

While the examples are based on achieving the dose of magnesium from MgO, the fill composition could include additional sources of magnesium, such as magnesium glycinate, magnesium citrate, magnesium chloride, magnesium sulfate, magnesium malate, etc. as sources of magnesium above and beyond the dose from the MgO.

Method of Treating a Subject in Need of a Magnesium Supplement

As used herein, a "subject" refers to a vertebrate, more particularly a mammal, for example, a human (or person) in need of a supplement to their diet, in particular, a supplement of magnesium. The method of treating a person in need of magnesium supplements includes identifying such a person and administering one softgel capsule having 400 mg magnesium from magnesium oxide that passed the dissolution test according to USP <711>. Numerous examples of softgel capsules with appropriate fill compositions were described herein and can be administered as a daily dose. The daily dose may be taken by the person for a period of days, weeks, months, or for the remainder of their life. Identifying the person in need of a magnesium supplement may include medical professional testing the person for a magnesium deficiency and determining that such a deficiency is present.

The above-detailed description of embodiments of the disclosure is not intended to be exhaustive or to limit the teachings to the precise form disclosed above. While specific embodiments of and examples for the disclosure are described above for illustrative purposes, various equivalent modifications are possible within the scope of the disclosure, as those skilled in the art will recognize and understand. For example, while processes can be presented in a given order, alternative embodiments can perform routines having steps in a different order, with some steps being deleted, moved, added, subdivided, combined, and/or modified to provide alternative or sub-combinations. Each of these processes can be implemented in a variety of different ways, as those skilled in the art will appreciate. Also, while processes are at times shown as being performed in series, these processes can instead be performed in parallel, or can be performed, at different times. Further, any specific numbers noted herein are only examples—alternative implementations can employ differing values or ranges.

The teachings of the disclosure provided herein can be applied to other systems, not necessarily the system described above. The elements and acts of the various embodiments described above can be combined to provide further embodiments. Any patents noted above that are incorporated herein by reference, for example, can be modified, as necessary, to provide yet further embodiments of the disclosure provided herein. Further, while the above description describes certain embodiments, the teachings can be practiced in many ways that will be appreciated by those of skill in the art no matter how detailed the above appears in the text. Details of the capsule members, capsules, and related processes and products can vary considerably in their implementation details, while still being encompassed by the subject matter disclosed herein. Hence, although example embodiments of the invention have been shown and described, it is to be understood that all the terms used herein are descriptive rather than limiting and that many changes, modifications, and substitutions can be made by one having skill in the art without departing from the spirit and scope of the claims below.

What is claimed is:

1. A softgel capsule comprising:

a fill composition comprising:

200 to 500 mg dose of magnesium from magnesium oxide;

55 to 70% w/w of an edible oil;

2 to 8% w/w polysorbate 80;

0.5 to 2% w/w hydrophobic silica; and 0.2 to 4% w/w of a chelating agent for binding to magnesium comprising ethylenediaminetetraacetic acid (EDTA) and/or an EDTA salt, and optionally a weak acid; and an outer softgel gelatin shell encapsulating the fill material;

wherein the softgel capsule has a dissolution according to United States Pharmacopeia (USP) <711> of greater than 75% for the magnesium oxide.

2. The softgel capsule of claim 1, wherein the weak acid is present and is ascorbic acid, aspartic acid, citric acid, glutamic acid, and/or pyridoxine hydrochloric acid (HCl).

3. The softgel capsule of claim 1, wherein the chelating agent comprises an ethylenediaminetetraacetic acid (EDTA) salt and a weak acid in a ratio of 2:1 to 2.5:1.

4. The softgel capsule of claim 3, wherein polysorbate 80 is present at about 6% to about 6.7% w/w of the fill composition.

5. The softgel capsule of claim 1, wherein the softgel capsules has a dissolution according to USP <711> of greater than 85%.

6. The softgel capsules of claim 1, wherein the edible oil comprises a medium-chain triglyceride oil.

7. The softgel capsule of claim 6, wherein the fill composition comprises:

50 to 65% w/w of the medium-chain triglyceride oil;

5.8 to 6.8% w/w of the polysorbate 80;

1 to 2% w/w of the hydrophobic silica; and 0.5 to 4% w/w of the chelating agent for binding to magnesium;

wherein the softgel capsule has a dissolution according to USP <711> of greater than 75%.

8. The softgel capsule of claim 7, wherein the softgel capsule has a dissolution according to USP <711> with Apparatus 1 of greater than 85% after six months at ambient condition; 75% after three months in an intermediate set at 30° C./65% relative humidity and one month in an accelerated condition chamber set at 40° C. and 75% relative humidity.

9. The softgel capsule of claim 7, wherein the softgel capsule has a dissolution according to USP <711> with Apparatus 2 of greater than 100% after six months at ambient condition and three months in an intermediate set at 30° C./65% relative humidity; and greater than 75% after a 4-month period in an accelerated condition chamber set at 40° C. and 75% relative humidity.

10. The softgel capsule of claim 7, wherein the chelating agent comprises the ethylenediaminetetraacetic acid (EDTA) salt and a weak acid.

11. The softgel capsule of claim 10, wherein the weak acid is present and is ascorbic acid, aspartic acid, citric acid, glutamic acid, and/or pyridoxine hydrochloric acid (HCl).

12. The softgel capsule of claim 7, wherein the chelating agent comprises an ethylenediaminetetraacetic acid (EDTA) salt and a weak acid in a ratio of 2:1 to 3:1.

* * * * *